(12) United States Patent
Pham et al.

(10) Patent No.: US 7,879,534 B2
(45) Date of Patent: Feb. 1, 2011

(54) FABRICATION OF A HIGH RESOLUTION BIOLOGICAL MOLECULE DETECTION DEVICE

(75) Inventors: Hong-An Pham, West Henrietta, NY (US); Dennis M. Connolly, Rochester, NY (US)

(73) Assignee: Integrated Nano-Technologies LLC, Henrietta, NY (US)

( * ) Notice: Subject to any disclaimer, the term of this patent is extended or adjusted under 35 U.S.C. 154(b) by 1628 days.

(21) Appl. No.: 10/496,454

(22) PCT Filed: Nov. 19, 2002

(86) PCT No.: PCT/US02/37258

§ 371 (c)(1), (2), (4) Date: Mar. 17, 2005

(87) PCT Pub. No.: WO04/001372

PCT Pub. Date: Dec. 31, 2003

(65) Prior Publication Data

US 2005/0186512 A1     Aug. 25, 2005

Related U.S. Application Data

(60) Provisional application No. 60/332,283, filed on Nov. 21, 2001.

(51) Int. Cl.
*C12N 11/00* (2006.01)
*C12Q 1/68* (2006.01)

(52) U.S. Cl. .................. 430/320; 430/323; 430/324; 422/68.1; 435/6; 435/7.1; 435/287.2; 435/174

(58) Field of Classification Search ................ None
See application file for complete search history.

(56) References Cited

U.S. PATENT DOCUMENTS

| 4,970,376 A | * | 11/1990 | Mellor et al. | 219/543 |
| 5,605,662 A | * | 2/1997 | Heller et al. | 422/68.1 |
| 2003/0040000 A1 | | 2/2003 | Connolly et al. | |

* cited by examiner

*Primary Examiner*—Daborah Chacko Davis
(74) *Attorney, Agent, or Firm*—Thomas R. FitzGerald, Esq.; Jason R. Womer, Esq.; Hiscock & Barclay, LLP (57) ABSTRACT

The present invention relates to a method of manufacturing a detection device which involves providing a substrate having a layer of electrically conductive material and a first layer of photosensitive material. Next, the substrate is subjected to a first level photolithography treatment to produce an electrical conductor containing conductive fingers with spaces between them. Finally, biological probes are attached to the conductive fingers under conditions effective to form a gap between the biological probes on the spaced apart conductive fingers, whereby a target molecule, if present in a sample, can bind to a pair of the biological probes on the spaced apart conductive fingers to bridge the gap between the biological probes, allowing detection of the target molecule.

20 Claims, 6 Drawing Sheets

FABRICATION OF A HIGH RESOLUTION BIOLOGICAL MOLECULE DETECTION DEVICE

This application claims the benefit of U.S. Provisional Patent Application Ser. No. 60/332,283, filed Nov. 21, 2001, which is hereby incorporated by reference in its entirety.

FIELD OF THE INVENTION

The present invention relates to methods of fabricating a device for the detection of target biological molecules from samples.

BACKGROUND OF THE INVENTION

For the analysis and testing of nucleic acid molecules, amplification of a small amount of nucleic acid molecules, isolation of the amplified nucleic acid fragments, and other procedures are necessary. The polymerase chain reaction method is widely used for the amplification of nucleic acid molecules, in which an extremely small number of nucleic acid molecules or fragments can be multiplied by several orders of magnitude to provide detectable amounts of material. On the other hand, isolation and detection of particular nucleic acid molecules in a mixture requires a nucleic acid sequencer and fragment analyzer, in which gel electrophoresis and fluorescence detection are combined. However, electrophoresis becomes very labor-intensive as the number of samples or test items increases. For this reason, a simpler method of analysis using DNA oligonucleotide probes is becoming popular. In this method, many kinds of oligonucleotide probes are immobilized on the surface of a solid to make a probe array. When contacted with a sample, only nucleic acid molecules with specific sequences matching the oligonucleotide are trapped on the surface of the solid and detected.

This kind of isolation and detection method, in which biological probes are immobilized on the surface of a solid and hybridization proceeds between the probes and a sample, has long been known as a blotting method in which the presence of the target molecule is detected by a probe immobilized on a membrane using radioactive labeling. However, immobilization of a large number of probes on a small area has the advantage that only a small amount of sample is required, and a large number of probes can be used simultaneously.

There are several methods for production of such products. Probe molecules can be synthesized one base at a time by a photochemical reaction on small segments of a solid using the same photomasking techniques used in the semiconductor industry. In another method, a synthesized DNA, a PCR-amplified DNA, or a protein molecule is immobilized on a small segment of the surface of a solid for each probe. A third method is to use an inkjet droplet to deposit the biological probe onto the surface. After the biological probes are attached to the surface, the sample containing the target molecule to be analyzed is passed over the biological probes at a temperature conducive to rapid hybridization of the target molecule with the probes. A washing solution then removes all the unhybridized, unbound molecules.

This method requires the use of fluorescent or radioactive labels as additional materials. Such a system is expensive to use and is not amenable to being made portable for biological sample detection and identification. Furthermore, the hybridization reactions can take up to two hours, which for many uses, such as detecting biological warfare agents, is simply too long. Therefore, a need exists for a device and system which can rapidly detect target molecules from samples.

The present invention is directed to achieving these objectives.

SUMMARY OF THE INVENTION

The present invention relates to a method of manufacturing a detection device. The method first involves providing a substrate having a layer of electrically conductive material between a first layer of photosensitive material and a base layer. Next, the substrate is subjected to a first level photolithography treatment to produce an electrical conductor containing conductive fingers with spaces between them. The spaces between the conductive fingers are covered with an electrical insulator material. Finally, biological probes are attached to the conductive fingers under conditions effective to form a gap between the biological probes on the spaced apart conductive fingers, where a target molecule, if present in a sample, can bind to a pair of the biological probes on the spaced apart conductive fingers. This bridges the gap between the biological probes, allowing detection of the target molecule.

Another aspect of the present invention relates to a method of manufacturing a detection device, which first involves providing a substrate having a base layer. Next, a first layer of electrical insulator material is deposited on one side of the base layer. A coating of adhesive material is then applied onto the first layer of electrical insulator material. Next, a layer of electrically conductive material is deposited on the coating of adhesive material. A first layer of photosensitive material is then coated onto the layer of electrically conductive material. Next, certain portions of the first layer of photosensitive material are exposed to ultraviolet light through a first photomask, and the first layer of photosensitive material is developed and baked, leaving portions of the layer of electrically conductive material uncovered. Then, the uncovered portions of the layer of electrically conductive material are removed from the substrate, leaving portions of the coating of adhesive material uncovered. Next, the uncovered portions of the coating of adhesive material are removed from the substrate. The photosensitive material remaining on the layer of electrically conductive material is then removed. Next, a second layer of an electrical insulator material is deposited on the substrate, and a second layer of photosensitive material is coated onto the second layer of electrical insulator material. Then, the second layer of photosensitive material is exposed to ultraviolet light through a second photomask, and the second layer of photosensitive material is developed and baked, leaving portions of the second layer of electrical insulator material uncovered. Next, the uncovered portions of the second layer of electrical insulator material are removed from the layer of electrically conductive material, where the exposing the second layer of photosensitive material, the developing and baking the second layer of photosensitive material, and the removing the uncovered portions of the second layer of electrical insulator material are carried out such that only portions of the second layer of electrical insulator material aligned with the conductive fingers will be removed, leaving portions of the second layer of photosensitive material on the substrate. The second layer of photosensitive material remaining on the second layer of electrical insulator material is then removed. Finally, biological probes are attached to the conductive fingers under conditions effective to form a gap between the biological probes on the spaced apart conductive fingers. As a result, a target molecule, if present in a sample, can bind to a pair of the biological probes on spaced apart conductive fingers to bridge the gap between the biological probes, allowing detection of the target molecule.

The present invention also relates to a method of manufacturing a detection device, which involves providing a substrate having an electrical conductor containing a plurality of coplanar conductive fingers with spaces between them, where the spaces are covered with an electrical insulator material. Biological probes are then attached to the conductive fingers under conditions effective to form a gap, between probes on the spaced apart, coplanar, conductive fingers. As a result, a target molecule, if present in a sample, can bind to a pair of the biological probes on spaced apart, coplanar, conductive fingers to bridge the gap between the biological probes, allowing detection of the target molecule.

Another aspect of the present invention relates to a method of manufacturing a detection device. The method first involves providing a substrate having a layer of electrically conductive material and a first layer of photosensitive material. Then, the substrate is subjected to a first level photolithography treatment to produce an electrical conductor having conductive fingers with spaces between them. Finally, biological probes are attached to the conductive fingers under conditions effective to form a gap between the biological probes on the spaced apart conductive fingers. As a result, a target molecule, if present in a sample, can bind to a pair of the biological probes on the spaced apart conductive fingers to bridge the gap between the biological probes, allowing detection of the target molecule.

The present invention provides methods of fabricating a device for rapidly detecting the presence of biological material. The target molecule either itself or as a support is used to complete an electrical circuit. The presence of the target molecule is indicated by the ability to conduct an electrical signal through the circuit. In the case where the target molecule is not present, the circuit will not be completed. Thus, the target molecule acts as a switch The presence of the target molecule provides an "on" signal for an electrical circuit, whereas the lack of the target molecule is interpreted as an "off" signal. Due to the direct detection of the target molecule, the device allows for extremely sensitive detection of target molecules connecting two electrical conductors.

BRIEF DESCRIPTION OF THE DRAWINGS

FIGS. 1A-R illustrate the sequence of steps necessary for fabricating a device for detecting the presence of a target molecule.

DETAILED DESCRIPTION OF THE INVENTION

The present invention relates to a method of manufacturing a detection device. The method first involves providing a substrate having a layer of electrically conductive material between a first layer of photosensitive material and a base layer. Next, the substrate is subjected to a first level photolithography treatment to produce an electrical conductor containing conductive fingers with spaces between them. The spaces between the conductive fingers are covered with an electrical insulator material. Finally, biological probes are attached to the conductive fingers under conditions effective to form a gap between the biological probes on the spaced apart conductive fingers, where a target molecule, if present in a sample, can bind to a pair of the biological probes on the spaced apart conductive fingers. This bridges the gap between the biological probes, allowing detection of the target molecule.

Another aspect of the present invention relates to a method of manufacturing a detection device, which first involves providing a substrate having a base layer. Next, a first layer of electrical insulator material is deposited on one side of the base layer. A coating of adhesive material is then applied onto the first layer of electrical insulator material. Next, a layer of electrically conductive material is deposited on the coating of adhesive material. A first layer of photosensitive material is then coated onto the layer of electrically conductive material. Next, certain portions of the first layer of photosensitive material are exposed to ultraviolet light through a first photomask, and the first layer of photosensitive material is developed and baked, leaving portions of the layer of electrically conductive material uncovered. Then, the uncovered portions of the layer of electrically conductive material are removed from the substrate, leaving portions of the coating of adhesive material uncovered. Next, the uncovered portions of the coating of adhesive material are removed from the substrate. The photosensitive material remaining on the layer of electrically conductive material is then removed. Next, a second layer of an electrical insulator material is deposited on the substrate, and a second layer of photosensitive material is coated onto the second layer of electrical insulator material. Then, the second layer of photosensitive material is exposed to ultraviolet light through a second photomask, and the second layer of photosensitive material is developed and baked, leaving portions of the second layer of electrical insulator material uncovered. Next, the uncovered portions of the second layer of electrical insulator material are removed from the layer of electrically conductive material, where the exposing the second layer of photosensitive material, the developing and baking the second layer of photosensitive material, and the removing the uncovered portions of the second layer of electrical insulator material are carried out such that only portions of the second layer of electrical insulator material aligned with the conductive fingers will be removed, leaving portions of the second layer of photosensitive material on the substrate. The second layer of photosensitive material remaining on the second layer of electrical insulator material is then removed. Finally, biological probes are attached to the conductive fingers under conditions effective to form a gap between the biological probes on the spaced apart conductive fingers. As a result, a target molecule, if present in a sample, can bind to a pair of the biological probes on spaced apart conductive fingers to bridge the gap between the biological probes, allowing detection of the target molecule.

The present invention also relates to a method of manufacturing a detection device, which involves providing a substrate having an electrical conductor containing a plurality of coplanar conductive fingers with spaces between them, where the spaces are covered with an electrical insulator material. Biological probes are then attached to the conductive fingers under conditions effective to form a gap between probes on the spaced apart, coplanar, conductive fingers. As a result, a target molecule, if present in a sample, can bind to a pair of the biological probes on spaced apart, coplanar, conductive fingers to bridge the gap between the biological probes, allowing detection of the target molecule.

Another aspect of the present invention relates to a method of manufacturing a detection device. The method first involves providing a substrate having a layer of electrically conductive material and a first layer of photosensitive material. Then, the substrate is subjected to a first level photolithography treatment to produce an electrical conductor having conductive fingers with spaces between them. Finally, biological probes are attached to the conductive fingers under conditions effective to form a gap between the biological probes on the spaced apart conductive fingers. As a result, a target molecule, if present in a sample, can bind to a pair of the biological probes on the spaced apart conductive fingers to bridge the gap between the biological probes, allowing detection of the target molecule.

Figure 1A:
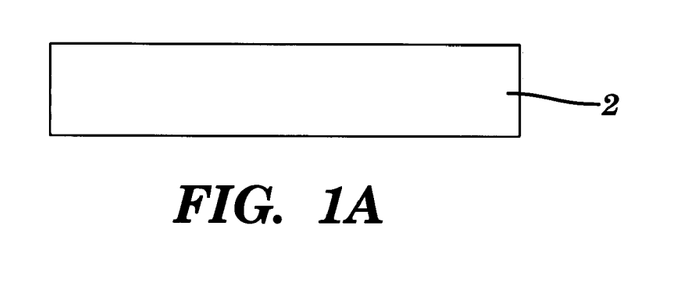
FIG. 1A depicts the cross sectional view of a substrate having a base layer.
Figure 1B:
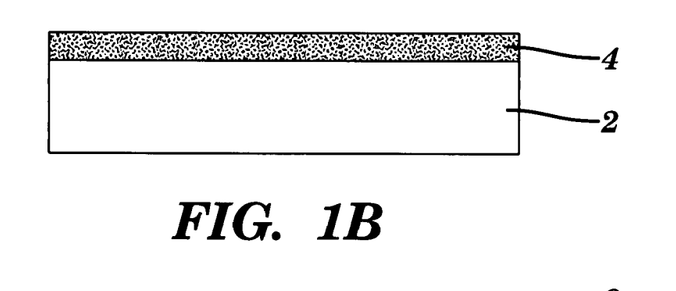
FIG. 1B is a cross sectional view of a substrate where a first layer of electrical insulator material has been deposited on one side of the base layer shown in FIG. 1A.
Figure 1C:
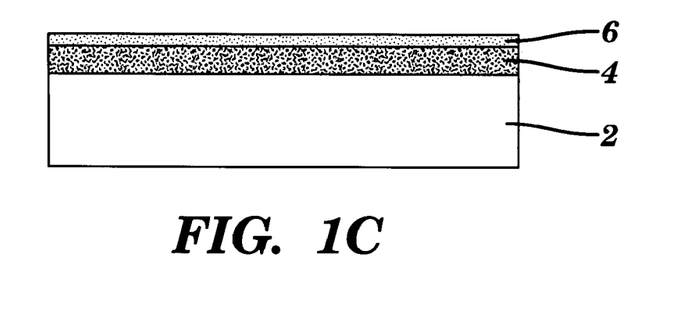
FIG. 1C shows the cross sectional view of a substrate where a coating of adhesive material has been applied onto the first layer of electrical insulator material shown in FIG. 1B.
Figure 1D:
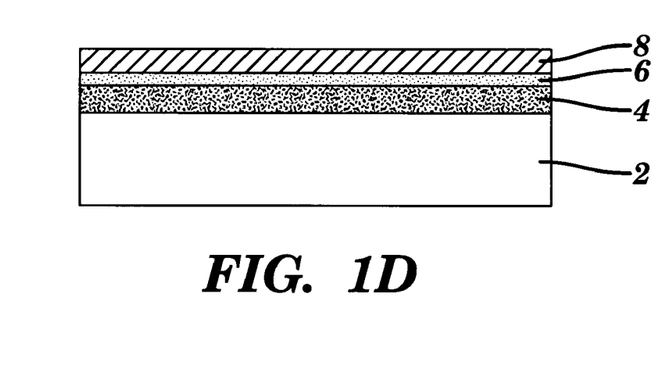
FIG. 1D illustrates the cross sectional view of a substrate where a layer of electrically conductive material has been deposited on the coating of adhesive material shown in FIG. 1C.
Figure 1E:
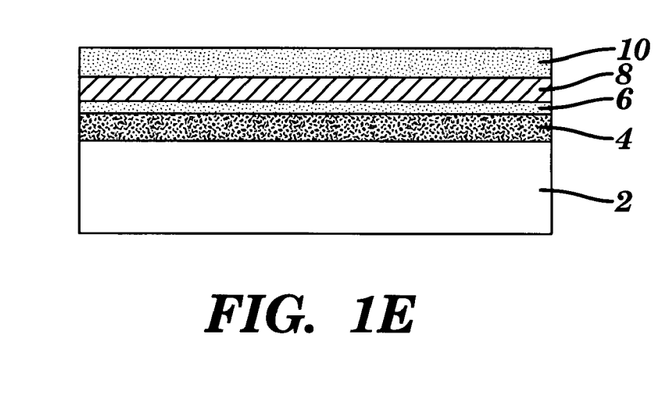
FIG. 1E depicts the cross sectional view of a substrate where a first layer of photosensitive material has been coated onto the layer of electrically conductive material shown in FIG. 1D.
Figure 1F:
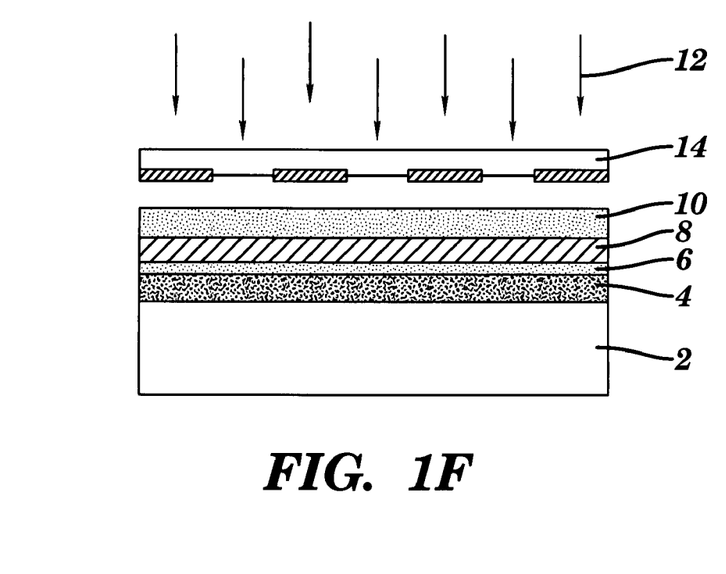
FIG. 1F shows the cross sectional view of a substrate where certain portions of the first layer of photosensitive material shown in FIG. 1E are exposed to ultraviolet light through a first photomask.
Figure 1G:
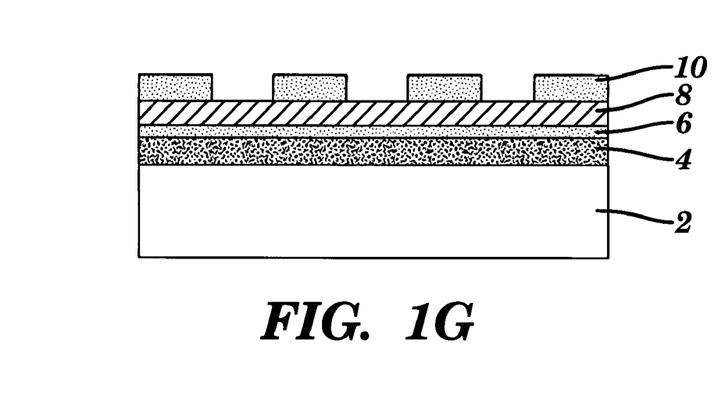
FIG. 1G is a cross sectional view of a substrate where the first layer of photosensitive material shown in FIG. 1F has been developed and baked, leaving portions of the layer of electrically conductive material uncovered.
Figure 1H:
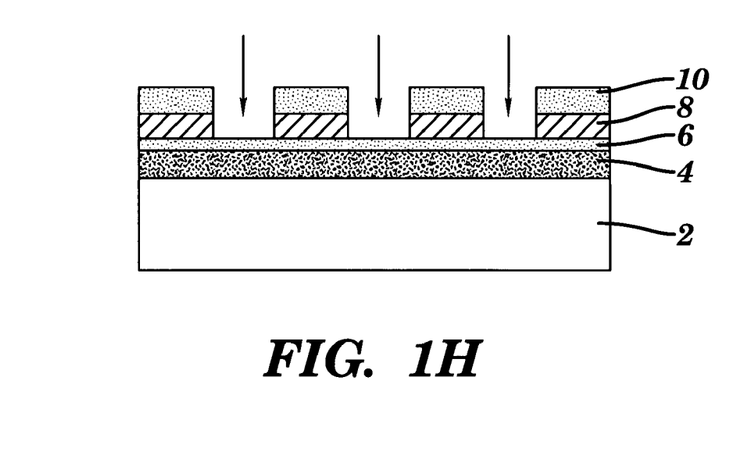
FIG. 1H illustrates the cross sectional view of a substrate where the uncovered portions of the layer of electrically conductive material shown in FIG. 1G has been removed, leaving portions of the coating of adhesive material uncovered.
Figure 1I:
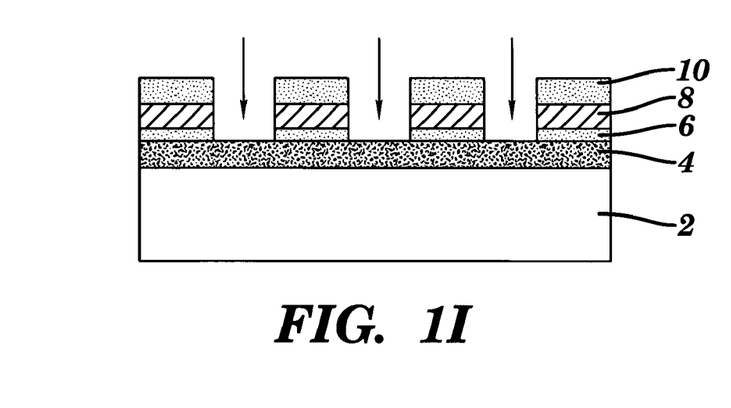
FIG. 1I depicts the cross sectional view of a substrate where the uncovered portions of the coating of adhesive material shown in FIG. 1H has been removed.
Figure 1J:
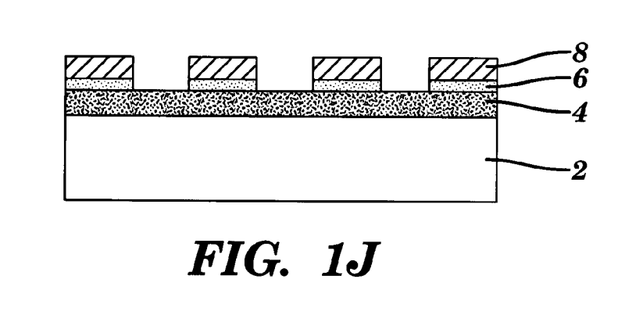
FIG. 1J is a cross sectional view of a substrate where the photosensitive material remaining on the layer of electrically conductive material shown in FIG. 1I has been removed.
Figure 1K:
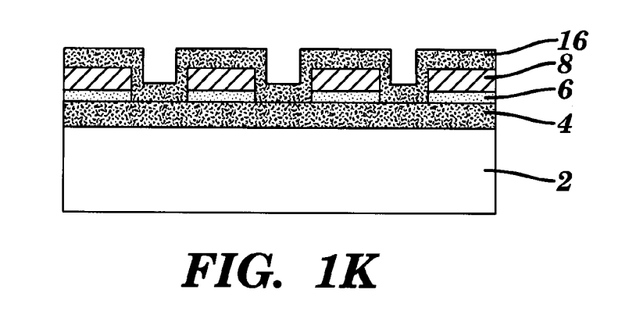
FIG. 1K shows the cross sectional view of a substrate where a second layer of an electrical insulator material has been deposited on the substrate shown in FIG. 1J.
Figure 1L:
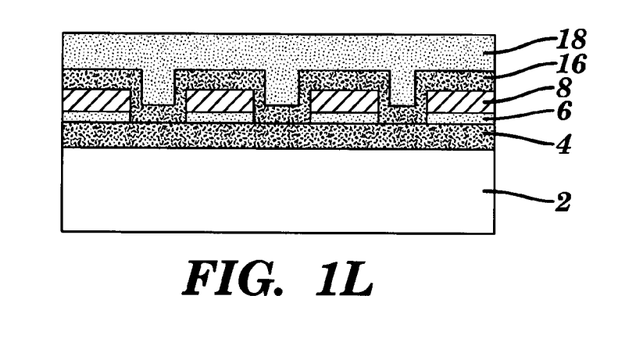
FIG. 1L illustrates the cross sectional view of a substrate where a second layer of photosensitive material has been coated onto the second layer of electrical insulator material shown in FIG. 1K.
Figure 1M:
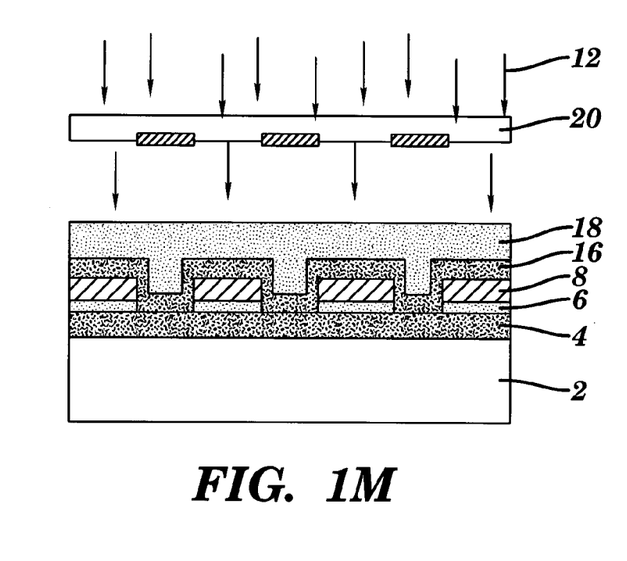
FIG. 1M depicts the cross sectional view of a substrate where the second layer of photosensitive material shown in FIG. 1L is being exposed to ultraviolet light through a second photomask.
Figure 1N:
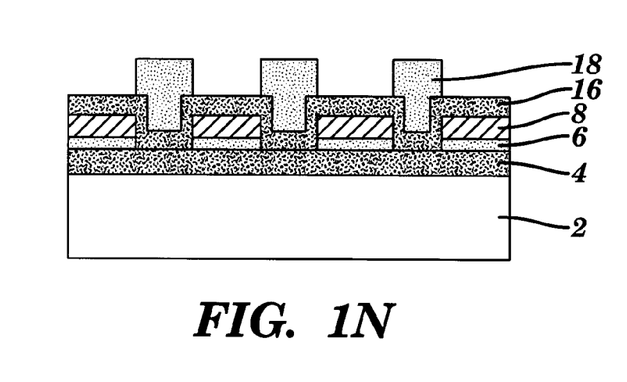
FIG. 1N is a cross sectional view of a substrate where the second layer of photosensitive material shown in FIG. 1M has been developed and baked, leaving portions of the second layer of electrical insulator material uncovered.
Figure 1O:
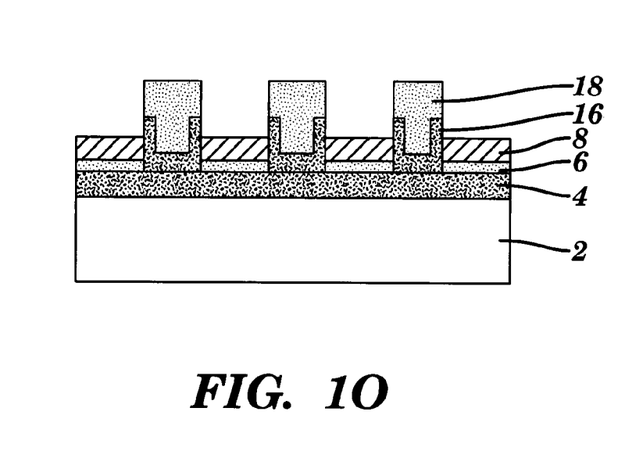
FIG. 1O shows the cross sectional view of a substrate where the uncovered portions of the second layer of electrical insulator material have been removed from the layer of electrically conductive material, leaving portions of the second layer of photosensitive material on the substrate.
Figure 1P:
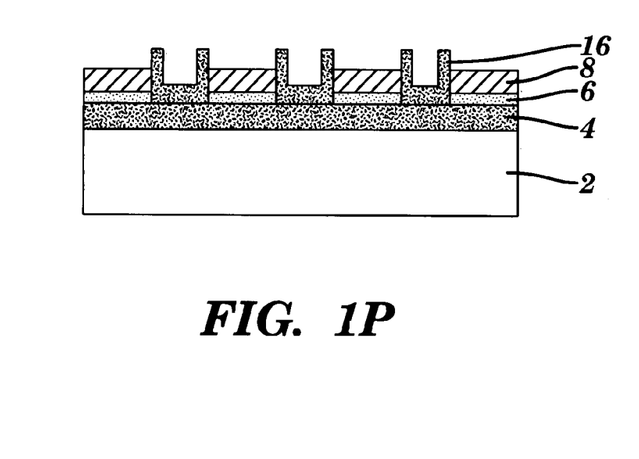
FIG. 1P illustrates the cross sectional view of a substrate where the second layer of photosensitive material remaining on the second layer of electrical insulator material shown in FIG. 1O has been removed.
Figure 1Q:
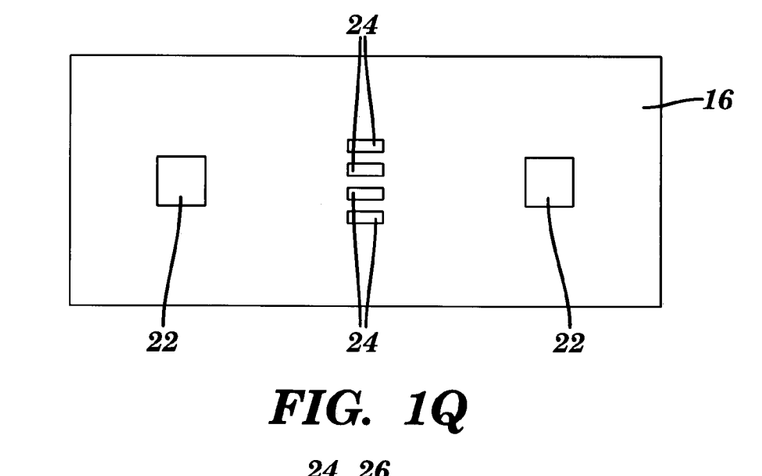
FIG. 1Q depicts the top view of the fabricated device before the biological probes are attached.
Figure 1R:
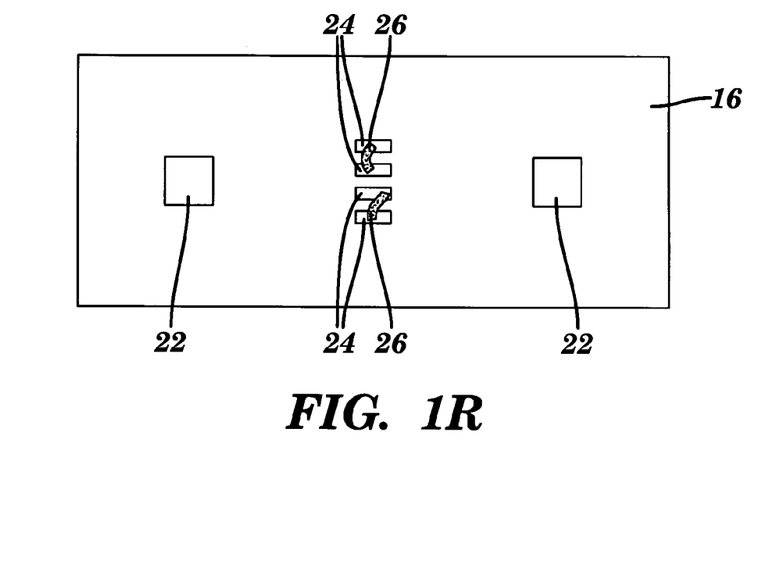
FIG. 1R shows the top view of the fabricated device after the biological probes are attached.

One embodiment of the method of the present invention is set forth in FIGS. 1A-R which depict the sequence of steps necessary for fabricating a device for detecting the presence of a target molecule.

This method first involves providing a substrate having base layer 2, as shown in FIG. 1A. An example of a suitable base layer material is silicon.

First layer of electrical insulator material 4 is deposited on one side of base layer 2, as shown in FIG. 1B. Examples of useful electrical insulator materials include silicon hard coat, silicon nitride, silicon dioxide, and polyimide.

Coating of adhesive material 6 is applied onto first layer of electrical insulator material 4, as shown in FIG. 1C. Examples of suitable adhesive materials are titanium, chromium, tungsten, and nickel.

Layer of electrically conductive material 8 is deposited on coating of adhesive material 6, as shown in FIG. 1D. While electrical conductors made of gold or aluminum are commonly used in the present invention, it is possible to use other materials as well. For example, metals such as titanium, tungsten, nickel, chromium, cobalt, and tantalum can be used as electrical conductors.

First layer of photosensitive material 10 is coated onto layer of electrically conductive material 8, as shown in FIG. 1E. Various photoresists, which are selected depending upon the exposing wavelength, can be used for this purpose.

Certain portions of first layer of photosensitive material 10 are exposed to ultraviolet light 12 through first photomask 14, as shown in FIG. 1F. Lithographic techniques used in the semiconductor manufacturing industries, such as photolithographic etching, plasma etching, or wet chemical etching, can be employed in the present invention. Alternatively, micromachining methods, such as laser drilling, micromilling and the like can be utilized.

First layer of photosensitive material 10 is developed and baked, leaving portions of layer of electrically conductive material 8 uncovered, as shown in FIG. 1G. Such development and baking is carried out by developing the exposed substrate in a base developer and hard baking on a hot plate.

Uncovered portions of layer of electrically conductive material 8 are removed from the substrate, leaving portions of coating of adhesive material 6 uncovered, as shown in FIG. 1H. Layer of electrically conductive material 8 is removed by etching the substrate with an etchant.

Uncovered portions of the coating of adhesive material 6 are removed from the substrate, as shown in FIG. 1I. This is achieved by using an etchant.

Photosensitive material 10 remaining on layer of electrically conductive material 8 is removed, as shown in FIG. 1J. This step can be carried out by using acetone. In one embodiment, portions of the first layer of photosensitive material that were exposed to ultraviolet light are removed. Alternatively, this step can be carried out such that the portions of the first layer of photosensitive material that were not exposed to ultraviolet light are removed.

Next, second layer of an electrical insulator material 16 is deposited on the substrate, as shown in FIG. 1K Suitable electrical insulator materials include silicon hard coat, silicon nitride, silicon dioxide, and polyimide.

Second layer of photosensitive material 18 is coated onto the second layer of electrical insulator material 16, as shown in FIG. 1L. Various photoresists, which are selected depending upon the exposing wavelength, can be used for this purpose.

Second layer of photosensitive material 18 is exposed to ultraviolet light 12 through a second photomask 20, as shown in FIG. 1M.

Exposed second layer of photosensitive material 18 is developed and baked, leaving portions of the second layer of electrical insulator material 16 uncovered, as shown in FIG. 1N. Such development and baking is carried out by developing the exposed substrate in a base developer and hard baling on a hot plate.

As shown in FIG. 1O, the uncovered portions of second layer of electrical insulator material 16 are removed from layer of electrically conductive material 8. This is carried out by plasma etching. Only portions of second layer of electrical insulator material 16 aligned with the conductive fingers are removed. Portions of second layer of photosensitive material 18 are left on the substrate, as shown in FIG. 1O.

Second layer of photosensitive material remaining 18 on second layer of electrical insulator material 16 is removed, as shown in FIG. 1P. This step can be carried out by using acetone. In one embodiment, portions of the second layer of photosensitive material that were exposed to ultraviolet light are removed. Alternatively, this step can be carried out such that the portions of the second layer of photosensitive material that were not exposed to ultraviolet light are removed.

The top view of the final fabricated device with two contact cuts 22 and an active area with spaced apart conductive fingers 24 exposed is shown in FIG. 1Q.

Finally, biological probes 26 are attached to conductive fingers 24 under conditions effective to form a gap between biological probes 26 on spaced apart conductive fingers 24, as shown in FIG. 1R. As a result, a target molecule, if present in a sample, can bind to a pair of the biological probes on spaced apart conductive fingers to bridge the gap between the biological probes, allowing detection of the target molecule. Details on methods of attaching biological molecules to electrically conductive surfaces can be found in U.S. Provisional Patent Application Ser. No. 60/310,937, filed on Aug. 8, 2001, which is hereby incorporated by reference in its entirety.

In one embodiment of the present invention, the biological probes are proteins or antibodies. FIG. 2 shows another embodiment of the present invention where the biological probes are oligonucleotide probes and the target molecule is a nucleic acid molecule. The oligonucleotide probes can be in the form of DNA, RNA, or protein nucleotide analogues. Such oligonucleotide probes are advantageously constructed from about 10 to 30 nucleotide bases. Shorter probe molecules have lower specificity for a target molecule, because there may exist in nature more than one target nucleic acid molecule with a sequence of nucleotides complementary to a shorter probe molecule. On the other hand, longer probe molecules have decreasingly small probabilities of complementary sequences with more than one natural target nucleic acid molecule. In addition, longer probe molecules exhibit longer hybridization times than shorter probe molecules. Since analysis time is a factor in a commercial device, the shortest possible probe that is sufficiently specific to the target nucleic acid molecule is desirable. Both the speed and specificity of binding target nucleic acid molecule to probe molecules can be increased if one electrical conductor has attached a probe molecule that is complementary to one end of the target nucleic acid molecule and the other electrical conductor has attached a probe that is complementary to the other end of the target nucleic acid molecule. In this case, even if short probe molecules that exhibit rapid hybridization rates are used, the specificity of the target molecule to the two probes is high.

Figure 2A:
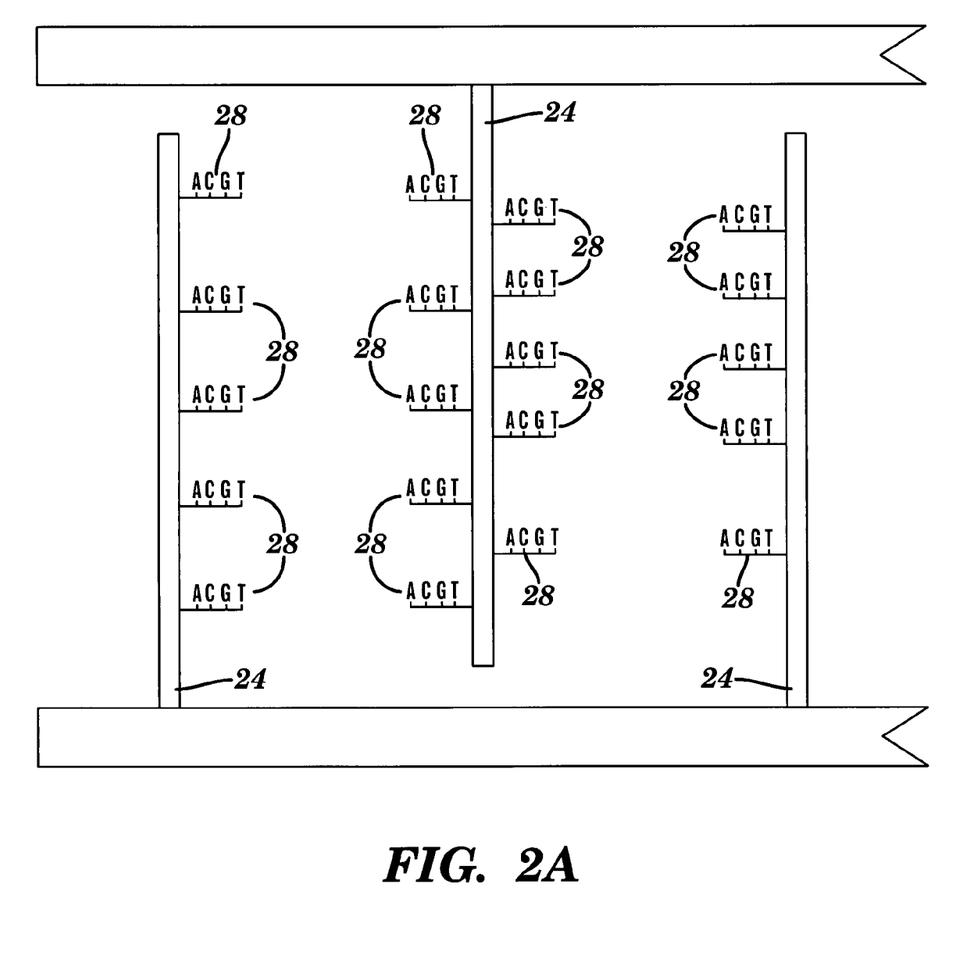
FIG. 2A illustrates an embodiment of the present invention where oligonucleotide probes are attached to the spaced part conductive fingers of the fabricated device shown in FIG. 1R.
Figure 2B:
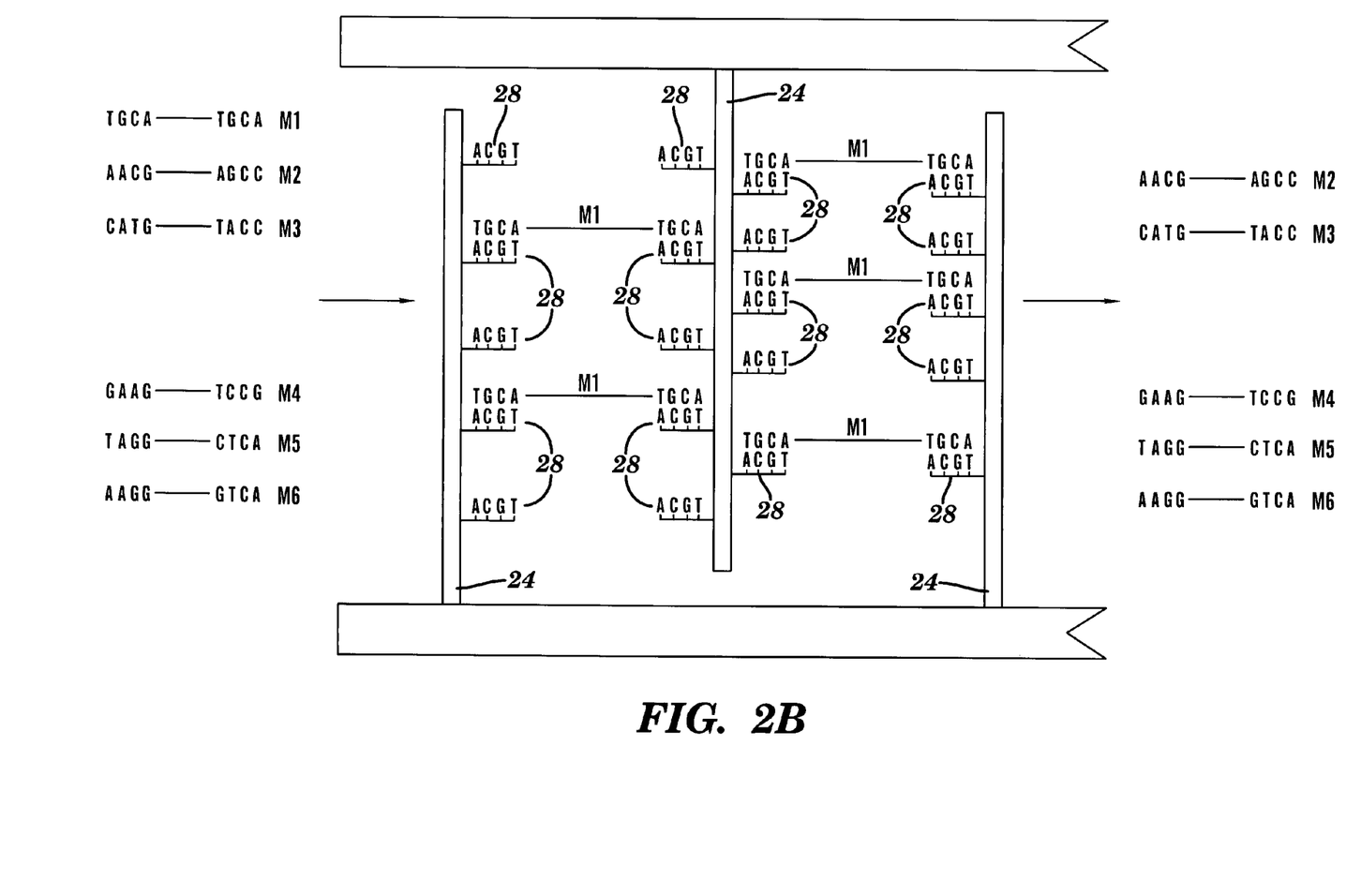
FIG. 2B shows how a target nucleic acid molecule present in a sample is detected by the fabricated device shown in FIG. 1R.

The fabricated device of the present invention is used to detect target molecules from samples. As shown in FIG. 2A, oligonucleotide probes 28 attached to the spaced apart conductive fingers 24 are physically located at a distance sufficient that they cannot come into contact with one another. A sample, containing a mixture of nucleic acid molecules (i.e. M1-M6), to be tested is contacted with the fabricated device on which conductive fingers 24 are fixed, as shown in FIG. 2B. If a target nucleic acid molecule (i.e. M1) which is capable of binding to the two oligonucleotide probes is present in the sample, the target nucleic acid molecule can electrically connect the two probes. Any unhybridized nucleic acid molecules (i.e. M2-M6) not captured by the probes is washed away. Here, the electrical conductivity of nucleic acid molecules is relied upon to transmit the electrical signal. Hans-Werner Fink and Christian Schoenenberger reported in *Nature* (1999), which is hereby incorporated by reference in its entirety, that DNA conducts electricity like a semiconductor. This flow of current can be sufficient to construct a simple switch, which will indicate whether or not a target nucleic acid molecule is present within a sample. The presence of a target molecule can be detected as an "on" switch, while a set of probes not connected by a target molecule would be an "off" switch. The information can be processed by a digital computer which correlates the status of the switch with the presence of a particular target. The information can be quickly identified to the user as indicating the presence or absence of the biological material, organism, mutation, or other target of interest.

Optionally, after hybridization of the target molecules to sets of biological probes, the target molecule can be coated with a conductor, such as a metal, as described in U.S. Patent Application Ser. Nos. 60/095,096 or 60/099,506, which are hereby incorporated by reference in their entirety. The coated target molecule can then conduct electricity across the gap between the pair of probes, thus producing a detectable signal indicative of the presence of a target molecule.

EXAMPLES

The following examples are provided to illustrate embodiments of the present invention but are by no means intended to limit its scope.

Example 1

Fabrication of a Detection Device With Gold Electrical Conductors

Fabrication began with a bare 6" silicon wafer (n-type or p-type) with (100) orientation, a resistivity of 5-15 ohm·cm, and a thickness of 675±50 μm.

A layer of silicon hard coat, as a first electrical insulator layer, was spin-coated on one side of the silicon wafer. A puddle of silicon hard coat (methylsilsesquioxane solution; SHC1200, GE Silicones, Waterford, N.Y.), about 3 inches in diameter, was dispensed onto the wafer, which was then spun at 3000 rpm for 180 sec and hard baked at 130° C. for 3 min.

A coating of chrome, as an adhesive layer, was evaporated onto the silicon hard coat. Once the evaporator (CVC, Port Townsend, Wash.) was at an appropriate pressure (low $10^{-6}$ Torr), one rod of chrome was evaporated for 10 sec. The chrome rod went from a glow to being very bright, with the chrome looking like it was peeling away, at which point the shutter was opened and the timer was started for 10 sec.

A layer of gold was deposited on the chrome. Once the evaporator (CVC, Port Townsend, Wash.) was at an appropriate pressure (low $10^{-6}$ Torr), a gold pellet (0.112 g) was evaporated to completion (approximately 20 sec). The shutter was not opened until the solid gold pieces melted. At this point, the deposited chrome/gold profile was around 300-500 Å.

A first layer of photoresist was coated onto the gold layer. The wafer was coated using coat trac or was hand-coated using Oir 620, a positive photoresist containing novalac resin, diazonaphthoquinone, casting solvent, additives, and surfactants (Olin, Norwalk, Conn.). When hand-coating, the substrate must be dehydration baked at 200° C. for 2 min on a hot plate, the photoresist must be dispensed at 4500 rpm for 1 min, and the substrate must be soft baked at 90° C. for 1 min on a hot plate.

The substrate was subjected to a first level lithography treatment, using an i-line stepper (Canon, Japan). The stepper job was loaded using the command, "ST DNA3_level 1." The exposure dose was set at 140-190 mj/cm$^2$ and the wavelength at 365 nm.

The exposed wafer was developed in a base developer (Shipley CD26, Shipley, Marboro, Mass.) for 1 min and rinsed with water. The wafer was dried and hard baked on a hot plate at 120° C. for 2 min.

The exposed gold was removed by etching the wafer with gold etchant (a mixture of iodine complex, potassium iodide, and water). The gold etching was carried out by first diluting the gold etchant (Transene type TFA, Danvers, Mass.) in a 2:1 (water etchant) solution. Then, the gold was etched for 5 sec in the gold etchant, using light to mild agitation. The wafer was removed from the pool of etchant after 1 sec, and then placed in a pool of DI water to remove the bulk of the etchant. The dish was emptied, refilled with DI water, and allowed to sit for a minute or so. Finally, the wafer was spin dried at 2000-2500 rpm for 30 sec.

The exposed chrome was removed by etching the wafer with chrome etchant (i.e. a mixture of ceric ammonium nitrate and acetic acid). Chrome etching was carried out by using the chrome etchant (Cyantek CE8002-A, Rowley, Mass.) for 10 sec, under light to mild agitation. The wafer was removed from the pool of etchant after 1 sec, and then placed in a pool of DI water to remove bulk of the etchant. Then, the dish was emptied, refilled with DI water, and allowed to sit for a minute or so. Finally, the wafer was spin dried at 2000-2500 rpm for 30 sec.

The photoresist remaining on the gold layer was removed. Before stripping the photoresist, the areas around the device were checked with an ohmmeter to see if the chrome cleared. The photoresist was removed with acetone and isopropanol. The wafer was rinsed with DI water and then spin dried at 2000-2500 rpm for 1 min.

A diamond film, as a second electrical insulator layer, was spin-coated onto the substrate.

The substrate was then coated with photoresist as previously described.

The substrate was subjected to a second level lithography treatment to open active areas and contact cuts, using an i-line stepper (Canon, Japan). The stepper job was loaded using the command, "ST DNA3_level 1." The substrate was exposed and a post-exposure bake was performed as described for the first level lithography. An exposure dose of 135-150 mj/cm$^2$ was used, although the exposure dose did not matter too much, because the second level critical dimension is relatively large compared to the first level CD.

The exposed substrate was developed in the base developer for 1 min and rinsed with water. The substrate can be developed on an SSI Manufacturer track or can be hand-developed in which case the photoresist should be hard-baked at 160° C. for 5 min. This high temperature hard bake induces cross-linking in the photoresist, making it more durable during further chemistry. The substrate was dried and hard baked on a hot plate at 120° C. for 2 min.

Next, the exposed diamond film was removed by plasma etching. This step is not necessary if photoresist is used as the second electrical insulator layer.

Next, the photoresist remaining on the gold layer was removed with acetone. This step is not necessary if photoresist is used as the second electrical insulator layer.

Finally, biological probe molecules are attached to the active area of the fabricated device with the gold electrical conductors exposed.

Example 2

Fabrication of a Detection Device With Aluminum Electrical Conductors

Fabrication began with a bare 6" silicon wafer (n-type or p-type) with (100) orientation, a resistivity of 5-15 ohm·cm, and a thickness of 675±50 μm.

A layer of silicon hard coat, as a first electrical insulator layer, was spin-coated on one side of the silicon wafer. A puddle of silicon hard coat (methylsilsesquioxane solution; SHC1200, GE Silicones, Waterford, N.Y.), about 3 inches in diameter, was dispensed onto the wafer, which was then spun at 3000 rpm for 180 sec.

A layer of aluminum was either sputtered or evaporated to the desired thickness onto the layer of silicon hard coat. When sputtered, power was set at 2000 Watts, argon flow at 63 sccm, presputter time at 5 min, chamber pressure at $10^{-6}$ Torr, deposition pressure at 5 mTorr, and deposition rate at 240 A/min. Alternatively, an aluminum pellet was evaporated using the evaporator (CVC, Port Townsend, Wash.) set at an appropriate chamber pressure (low $10^{-6}$ Torr) to give an approximate thickness of 2000 Å.

A first layer of photoresist was coated onto the aluminum layer. The wafer was coated using coat trac or was hand-coated using Oir 620, a positive photoresist containing novalac resin, diazonaphthoquinone, casting solvent, additives, and surfactants (Olin, Norwalk, Conn.). When hand-coating, the substrate must be dehydration baked at 200° C. for 2 min on a hot plate, the photoresist must be dispensed at 4500 rpm for 1 min, and the substrate must be soft baked at 90° C. for 1 min on a hot plate.

The substrate was subjected to a first level lithography treatment, using an i-line stepper (Canon, Japan). The stepper job was loaded using the command, "ST DNA3_level 1." The exposure dose was set at 130 mj/cm$^2$.

The exposed wafer was developed in a base developer (Shipley CD26, Shipley, Marboro, Mass.) for 1 min and rinsed with water. The wafer was dried and hard baked on a hot plate at 120° C. for 2 min.

The exposed aluminum was removed by etching the wafer with aluminum etchant at 50° C., and rinsing well in DI water. The etching time depended on the thickness of aluminum, and the etch rate was 2000 Å/min.

The photoresist remaining on the aluminum layer was removed with acetone and rinsed with DI water.

A diamond film, as a second electrical insulator layer, was spin-coated onto the substrate.

The substrate was then coated with photoresist as previously described.

The substrate was subjected to a second level lithography treatment to open active areas and contact cuts, using an i-line stepper (Canon, Japan). The stepper job was loaded using the command, "ST DNA3_level 1." The substrate was exposed and a post-exposure bake was performed as described for the first level lithography. An exposure dose of 130 mj/cm$^2$ was used.

The exposed substrate was developed in the base developer for 1 min and rinsed with water. Then, the substrate was dried and hard baked on a hot plate at 120° C. for 2 min.

Next, the exposed diamond film was removed by plasma etching in $O_2$. This step is not necessary if photoresist is used as the second electrical insulator layer.

Next, the photoresist remaining on the aluminum layer was removed with acetone. This step is not necessary if photoresist is used as the second electrical insulator layer.

Finally, biological probe molecules are attached to the active area of the fabricated device with the aluminum electrical conductors exposed.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of manufacturing a detection device comprising:
    providing a substrate having a layer of electrically conductive material between a layer of photosensitive material and a base layer,
    subjecting the substrate to a photolithography treatment to produce an electrical conductor comprising conductive fingers with spaces between them; and
    attaching biological probes to the conductive fingers under conditions effective to form a gap between the biological probes on the spaced apart conductive fingers, whereby a target molecule, if present in a sample, can bind to a pair of the biological probes on the spaced apart conductive fingers to bridge the gap between the biological probes, allowing detection of the target molecule;
    wherein said substrate further comprises:
        a first layer of electrical insulator material between the base layer and the layer of electrically conductive material; and
        a coating of adhesive material between the layer of electrical insulator material and the layer of electrically conductive material.

2. A method according to claim 1, wherein said providing a substrate comprises:
    depositing the layer of electrical insulator material on one side of the base layer;
    applying the coating of adhesive material onto the layer of electrical insulator material;
    depositing the layer of electrically conductive material on the coating of adhesive material; and
    coating the layer of photosensitive material onto the layer of electrically conductive material.

3. A method according to claim 1, wherein said subjecting the substrate to photolithography treatment comprises:
    exposing certain portions of the layer of photosensitive material to ultraviolet light through a first photomask;
    developing and baking the layer of photosensitive material leaving portions of the layer of electrically conductive material uncovered;
    removing the uncovered portions of the layer of electrically conductive material from said substrate, leaving portions of the coating of adhesive material uncovered;
    removing the uncovered portions of the coating of adhesive material from said substrate; and
    removing the photosensitive material remaining on the layer of electrically conductive material.

4. A method according to claim 3, wherein said method is carried out such that the portions of the layer of photosensitive material that were exposed to ultraviolet light are removed.

5. A method according to claim 3, wherein said method is carried out such that the portions of the layer of photosensitive material that were not exposed to ultraviolet light are removed.

6. A method of manufacturing a detection device, said method comprising:
    providing a substrate having a base layer;
    depositing a first layer of electrical insulator material on one side of the base layer;
    applying a coating of adhesive material onto the first layer of electrical insulator material;
    depositing a layer of electrically conductive material on the coating of adhesive material;
    coating a first layer of photosensitive material onto the layer of electrically conductive material;
    exposing certain portions of the first layer of photosensitive material to ultraviolet light through a first photomask;
    developing and baking the first layer of photosensitive material, leaving portions of the layer of electrically conductive material uncovered;
    removing the uncovered portions of the layer of electrically conductive material from said substrate, forming spaced apart conductive fingers, leaving portions of the coating of adhesive material uncovered;
    removing the uncovered portions of the coating of adhesive material from said substrate;
    removing the portions of the first photosensitive material remaining on the layer of electrically conductive material;
    depositing a second layer of an electrical insulator material on said substrate; coating a second layer of photosensitive material onto the second layer of electrical insulator material;
    exposing the second layer of photosensitive material to ultraviolet light through a second photomask;
    developing and baking the second layer of photosensitive material, leaving portions of the second layer of electrical insulator material uncovered;
    removing the uncovered portions of the second layer of electrical insulator material from said layer of electrically conductive material, wherein said exposing the second layer of photosensitive material, said developing and baking the second layer of photosensitive material, and said removing the uncovered portions of the second layer of electrical insulator material are carried out such that only portions of the second layer of electrical insulator material aligned with the spaced apart conductive fingers will be removed, leaving portions of the second layer of photosensitive material on the substrate; and
    removing the second layer of photosensitive material remaining on the second layer of electrical insulator material; and
    attaching biological probes to the spaced apart conductive fingers under conditions effective to form a gap between the biological probes on the spaced apart conductive fingers, whereby a target molecule, if present in a sample, can bind to a pair of the biological probes on the spaced apart conductive fingers to bridge the gap between the biological probes, allowing detection of the target molecule.

7. A method according to claim 6, wherein the biological probes are oligonucleotide probes and the target molecule is a nucleic acid molecule.

8. A method according to claim 6, wherein the biological probes are proteins or antibodies.

9. A method according to claim 6, wherein said method is carried out such that the portions of the first layer of photosensitive material that were exposed to ultraviolet light are removed.

10. A method according to claim 6, wherein said method is carried out such that the portions of the first layer of photosensitive material that were not exposed to ultraviolet light are removed.

11. A method according to claim 6, wherein said method is carried out such that the portions of the second layer of photosensitive material that were exposed to ultraviolet light are removed.

12. A method according to claim 6, wherein said method is carried out such that the portions of the second layer of photosensitive material that were not exposed to ultraviolet light are removed.

13. A method of manufacturing a detection device, said method comprising:
providing a substrate having an electrical conductor comprising a plurality of coplanar conductive fingers with spaces between them;
the detection device comprising an electrical insulator material between the substrate and the electrical conductor; and
an adhesive material between the electrical insulator material and the electrical conductor; and
attaching biological probes to the conductive fingers under conditions effective to form a gap between probes on the spaced apart, coplanar, conductive fingers, whereby a target molecule, if present in a sample, can bind to a pair of the biological probes on spaced apart, coplanar, conductive fingers to bridge the gap between the biological probes, allowing detection of the target molecule.

14. A method according to claim 13, wherein the biological probes are oligonucleotide probes and the target molecule is a nucleic acid molecule.

15. A method according to claim 13, wherein the biological probes are proteins or antibodies.

16. A method of manufacturing a detection device comprising:
providing a substrate having a layer of electrically conductive material, a layer of photosensitive material, an electrical insulator material between the substrate and the electrically conductive material and an adhesive material between the electrical insulator material and the electrically conductive material;
subjecting the substrate to a photolithography treatment to produce an electrical conductor comprising conductive fingers with spaces between them; and
attaching biological probes to the conductive fingers under conditions effective to form a gap between the biological probes on the spaced apart conductive fingers, whereby a target molecule, if present in a sample, can bind to a pair of the biological probes on the spaced apart conductive fingers to bridge the gap between the biological probes, allowing detection of the target molecule.

17. A method according to claim 16, wherein said substrate further comprises a base layer wherein said layer of electrically conductive material is between said layer of photosensitive material and said base layer.

18. A method according to claim 16, further comprising:
covering the spaces between the conductive fingers with an electrical insulator material prior to said attaching biological probes and after said subjecting the substrate to photolithography.

19. A method according to claim 16, wherein the biological probes are oligonucleotide probes and the target molecule is a nucleic acid molecule.

20. A method according to claim 16, wherein the biological probes are proteins or antibodies.

* * * * *